United States Patent
Amino et al.

(10) Patent No.: US 6,649,784 B2
(45) Date of Patent: Nov. 18, 2003

(54) ASPARTYL DIPEPTIDE ESTER DERIVATIVES AND SWEETENERS

(75) Inventors: Yusuke Amino, Kanagawa-ken (JP); Tadashi Takemoto, Kanagawa-ken (JP); Kazuko Yuzawa, Kanagawa-ken (JP); Ryoichiro Nakamura, Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/109,719

(22) Filed: Apr. 1, 2002

(65) Prior Publication Data
US 2003/0065210 A1 Apr. 3, 2003

Related U.S. Application Data

(63) Continuation of application No. PCT/JP00/06627, filed on Sep. 26, 2000.

(30) Foreign Application Priority Data

Oct. 1, 1999 (JP) ............................................ 11-281920

(51) Int. Cl.[7] ............................................ C07C 229/00

(52) U.S. Cl. ...................... 560/41; 465/548; 544/322; 558/413; 560/38

(58) Field of Search ..................... 560/41, 38; 426/548; 544/322; 558/413

(56) References Cited

U.S. PATENT DOCUMENTS

| | | | |
|---|---|---|---|
| 5,480,668 A | 1/1996 | Nofre et al. | |
| 5,723,165 A | 3/1998 | Takemoto et al. | |
| 5,723,651 A | 3/1998 | Hijiya et al. | |
| 5,795,612 A | 8/1998 | Takemoto et al. | |
| 5,958,496 A | 9/1999 | Amino et al. | |
| 5,968,581 A | 10/1999 | Nakamura et al. | |
| 6,010,733 A | 1/2000 | Takemoto et al. | |
| 6,335,461 B1 | 1/2002 | Amino et al. | |
| 6,548,096 B1 | 4/2003 | Amino et al. | |

FOREIGN PATENT DOCUMENTS

| | | | |
|---|---|---|---|
| AU | 9956501 | * | 3/2000 |
| WO | WO99/52937 | | 10/1999 |
| WO | WO00/00508 | | 1/2000 |
| WO | WO 0017230 | * | 3/2000 |

* cited by examiner

*Primary Examiner*—Alan L. Rotman
*Assistant Examiner*—Héctor M. Reyes
(74) *Attorney, Agent, or Firm*—Oblon, Spivak, McClelland, Maier & Neustadt, P.C.

(57) ABSTRACT

Aspartyl dipeptide ester derivatives, such as a N-[N-[3-(3,4-dihydroxyphenyl)-3-methylbutyl]-L-α-aspartyl]-L-phenylalanine 1-methyl ester, or salts thereof, having a high degree of sweetness compared to conventional sweeteners. These derivatives are excellent in sweetening potency and may be used as sweetener components in products such as foods and drinks. They may also be used as low calorie sweeteners and in methods of sweetening products. Foods and drinks comprising these derivatives as well as methods for their production.

28 Claims, No Drawings

ASPARTYL DIPEPTIDE ESTER DERIVATIVES AND SWEETENERS

CROSS-REFERENCE TO RELATED APPLICATIONS

This application is a continuation of PCT/JP00/06627, filed Sep. 26, 2000. This application is also related to and claims priority to JP 11/281920, filed Oct. 1, 1999.

BACKGROUND OF INVENTION

1. Field of the Invention

The present invention relates to novel aspartyl dipeptide ester derivatives that are safe, have a taste similar to that of sugar and a high degree of sweetness, for instance, to compounds which are at least 10,000-times sweeter than sugar. The invention also encompasses sweeteners comprising these aspartyl dipeptide ester derivatives, as well as products, such as foods and drinks, containing such sweeteners. Methods for making and using the sweeteners of the present invention are also described.

2. Description of the Related Art

In recent years, the development of low-calorie sweeteners has been demanded due to changes in eating habits, such as increased fatness caused by excessive intake of sugar, as well as due to the prevalence of various diseases associated with fatness.

Aspartame is a sweetener that is presently widely used and is excellent in terms of safety and for its sweetening qualities. However, the stability of aspartame is problematic.

Slight improvements in stability as well as improvements in sweetening potency have been reported for aspartame derivatives obtained by introducing an alkyl group into a nitrogen atom of aspartic acid in aspartame, see Kokai Publication of the International Patent WO 94/11391. Most excellent among compounds described in this Publication is N-[N-(3,3-dimethylbutyl)-L-α-aspartyl]-L-phenylalanine 1-methyl ester having a 3,3-dimethylbutyl group as an alkyl group, and the sweetening potency (degree of sweetness) is 10,000 times that of sucrose (compared with 2, 5 and 10% sucrose solutions).

Other aspartame derivatives having introduced therein 20 types of substituents other than the 3,3-dimethylbutyl group are also described. However, the sweetening potencies (degrees of sweetness) of all these derivatives has been reported to be not more than 2,500 times.

Derivatives having a 3-(substituted phenyl)propyl group as an alkyl group are also described. With respect to derivatives having a relatively high sweetening potency among them, it is reported that a sweetening potency of N-[N-(3-phenylpropyl)-L-α-aspartyl]-L-phenylalanine 1-methyl ester is 1,500 times and a sweetening potency of N-[N-[3-(3-methoxy-4-hydroxyphenyl)propyl]-L-α-aspartyl]-L-phenylalanine 1-methyl ester is 2,500 times. However, the sweetening potencies of these derivatives do not reach the potency (10,000 times that of sugar) of N-[N-(3,3-dimethylbutyl)-L-α-aspartyl]-L-phenylalanine 1-methyl ester.

Further, it is reported that the sweetening potency of N-[N-[(RS)-3-phenylbutyl]-L-α-aspartyl]-L-phenylalanine 1-methyl ester having a substituent of a structure that a methyl group is further introduced in the 3-position of a 3-phenylpropyl group, namely a 3-phenylbutyl group as an alkyl group is only 1,200 times. Thus, by introducing the methyl group in the 3-position, the sweetening potency is decreased in comparison with N-[N-(3-phenylpropyl)-L-α-aspartyl]-L-phenylalanine 1-methyl ester.

Thus, the development of sweeteners that solve the aforementioned problems and which are safe, taste like sugar, have greater stability, and/or have a much higher sweetening potency has been in demand.

BRIEF SUMMARY OF THE INVENTION

The present invention solves the problems of prior art sweeteners mentioned above, such as low sweetening potency, by providing a novel aspartyl dipeptide ester derivative excellent in safety, having a sweet taste similar to sugar and a sweetening potency which is equal to or higher than that of the N-[N-(3,3-dimethylbutyl)-L-α-aspartyl-L-phenylalanine 1-methyl ester described above. The invention also encompasses sweeteners, such as low-calorie sweeteners, and foods and drinks containing these more potent sweeteners.

DETAILED DESCRIPTION OF THE INVENTION

To solve the foregoing problems, the present inventors have synthesized various compounds in which various 3-(substituted phenyl)propyl groups, for example, a 3,3-dialkyl-3-(substituted phenyl)propyl group, are introduced into nitrogen of aspartic acid constituting aspartame by a reductive alkylation reaction using 3-phenylpropionaldehyde derivatives or cinnamaldehyde derivatives (including derivatives having an alkyl substituent in a main chain) having various substituents, especially two or more hydroxyl groups in a phenyl group, and have examined a sweetening potency thereof.

As a result, compounds have been discovered that have a sweetening potency which is by far higher than that of N-[N-(3,3-dimethylbutyl)-L-α-aspartyl]-L-phenylalanine 1-methyl ester, which has been reported to have a sweetening potency of 10,000 times in the foregoing Kokai Publication of the International Patent WO 94/11391, not to mention N-[N-[(RS)-3-phenylbutyl]-L-α-aspartyl]-L-phenylalanine 1-methyl ester reported therein to have a sweetening potency of 1,200 times, N-[N-3-(3-methoxy-4-hydroxyphenyl)propyl]-L-α-aspartyl]-L-phenylalanine 1-methyl ester reported therein to have a sweetening potency of 2,500 times, and the like.

In particular it has been found that compounds represented by the following general formula (1) are especially excellent as sweeteners and the present invention has been completed on the basis of this finding. That is, the present invention lies in aspartyl dipeptide ester derivatives represented by the following general formula (1) (including those in the form of salts), sweeteners and products, such as foods and drinks, and the like comprising the same, and in a method for imparting sweetness to various products.

Formula (1)

(1)

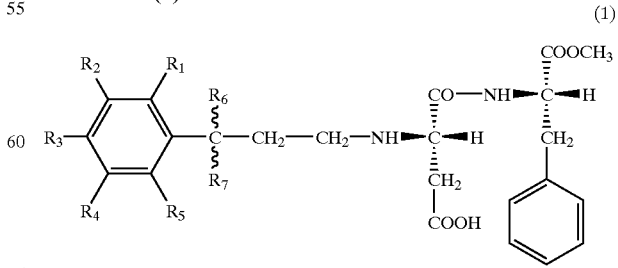

wherein $R_1$, $R_2$, $R_3$, $R_4$ and $R_5$ independently from each other, represent a hydrogen atom (H) or a hydroxyl group (OH), at least any two selected from $R_1$, $R_2$, $R_3$, $R_4$ and $R_5$ are hydroxyl groups, and $R_6$ and $R_7$, independently from each other, represent a hydrogen atom (H) or an alkyl group having 1 to 3 carbon atoms ($CH_3$, $CH_2CH_3$, $CH(CH_3)_2$ or the like).

When $R_6$ and $R_7$ represent different substituents, a steric configuration of a carbon atom to which these substituents are bound is not particularly limited, and it may be any of (R), (S) and (RS), or a mixed form of these plural forms. Incidentally, in the general formula (1) described above, the binding site (linkage) between $R_6$ or $R_7$ and the carbon atom is indicated by a wavy line, meaning that there are no limitations on the direction of linkage.

MODE FOR CARRYING OUT THE INVENTION

The compounds represented by the general formula (1) described above and those in the form of salts are both included in the novel aspartyl dipeptide ester derivatives of the present invention.

When they are incorporated in sweeteners and the like, it is advisable that at least one compound or at least one compound in the form of a salt is incorporated. Accordingly, one of the compounds or a mixture of more than one thereof, one of the salts of the compounds or a mixture of more than one thereof, a mixture of the compound(s) and the salt(s) of the compound(s), and the like can all be incorporated in sweetener(s), foods and drinks and the like of the present invention.

Amino acids (aspartic acid and phenylalanine) constituting the derivatives described above are both preferably L-isomers because they are present in nature.

With respect to the preferable forms of the compounds, the following inventions are included in the compounds of the present invention.

[1] Compounds represented by the general formula (1) described above.

In the general formula (1), $R_1$, $R_2$, $R_3$, $R_4$ and $R_5$, independently from each other, represent a hydrogen atom (H) or a hydroxyl group (OH), and at least any two selected from $R_1$, $R_2$, $R_3$, $R_4$ and $R_5$ are hydroxyl groups, and $R_6$ and $R_7$, independently from each other, represent a hydrogen atom (H) or an alkyl group having 1 to 3 carbon atoms ($CH_3$, $CH_2CH_3$, $CH(CH_3)_2$ or the like).

When $R_6$ and $R_7$ represent different substituents, a steric configuration of a carbon atom to which these substituents are bound is not particularly limited, and it may be any of (R), (S) and (RS).

[2] Compounds described in (1) above in which in the formula any two selected from $R_1$, $R_2$, $R_3$, $R_4$ and $R_5$ are hydroxyl groups.

[3] Compounds described in (1) above in which in the formula any three selected from $R_1$, $R_2$, $R_3$, $R_4$ and $R_5$ are hydroxyl groups.

[4] Compounds described in (1) above in which in the formula $R_6$ and $R_7$ are hydrogen atoms.

[5] Compounds described in (1) above in which in the formula $R_6$ is a methyl group.

[6] Compounds described in (1) above in which in the formula $R_7$ is a methyl group.

[7] Compounds described in (1) above in which in the formula $R_1$ and $R_3$ are hydroxyl groups, and $R_2$, $R_4$, $R_5$, $R_6$ and $R_7$ are hydrogen atoms.

[8] Compounds described in (1) above in which in the formula $R_2$ and $R_3$ are hydroxyl groups, and $R_1$, $R_4$, $R_5$, $R_6$ and $R_7$ are hydrogen atoms.

[9] Compounds described in (1) above in which in the formula $R_1$, $R_2$ and $R_3$ are hydroxyl groups, and $R_4$, $R_5$, $R_6$ and $R_7$ are hydrogen atoms.

[10] Compounds described in (1) above in which in the formula $R_2$, $R_3$ and $R_4$ are hydroxyl groups, and $R_1$, $R_5$, $R_6$ and $R_7$ are hydrogen atoms.

[11] Compounds described in (1) above in which in the formula $R_2$ and $R_3$ are hydroxyl groups, $R_1$, $R_4$ and $R_5$ are hydrogen atoms, and $R_6$ and $R_7$ are methyl groups.

[12] Compounds described in (1) above in which when $R_6$ and $R_7$ in the formula represent different substituents, the steric configuration of the carbon atom to which $R_6$ is bound is any of (R), (S) and (RS).

The present invention also includes the following inventions as preferable embodiments.

[13] Sweeteners, foods and drinks having a sweetness and other products having a sweetness, comprising the derivatives (including those in the form of salts) of the present invention as an active ingredient.

Further, a carrier and/or a filler (a bulking agent) for sweeteners may be contained therein. As described above, at least one of the derivatives described above can be contained in the sweeteners and the like described above.

[14] A method for imparting a sweetness (a sweet taste) wherein the derivative(s) of the present invention is contained (mixed or added) in products requiring a sweetness (foods and drinks, pharmaceuticals, oral sanitary products and the like) and intermediate products during the production stage thereof.

The method for using the derivatives of the present invention in the production stage of sweeteners, products and the like is not particularly limited, and it can be conducted using a method known as a method for using sweet ingredient(s) or various methods which will be developed in future.

The derivatives of the present invention include the compounds represented by the formula (1) or salts thereof. Examples of the salts of the compounds include salts with alkali metals such as sodium, potassium and the like, salts with alkaline earth metals such as calcium, magnesium and the like, ammonium salt with ammonia, salts with amino acids such as lysine, arginine and the like, salts with inorganic acids such as hydrochloric acid, sulfuric acid and the like, salts with organic acids such as citric acid, acetic acid and the like, and salts with other sweeteners such as saccharin, acesulfame, cyclamic acid, glycyrrhizic acid and the like. These are also included in the derivatives of the present invention as stated above.

It is not particularly difficult to produce the aspartyl dipeptide ester derivatives of the present invention. Preferably, they can easily be formed by reductively alkylating aspartame with 3-phenylpropionaldehyde derivatives or cinnamaldehyde derivatives (including derivatives having alkyl substituent(s) in a main chain) having various substituents in a phenyl group and a reducing agent (for example, hydrogen/palladium carbon catalyst). Alternatively, they can be formed by a method which comprises reductively alkylating aspartame derivatives (for example, β-O-benzyl-L-α-aspartyl-L-phenylalanine methyl ester) having a protecting group in a carboxyl group in the β-position which can be obtained according to an ordinary peptide synthesis method (refer to Izumiya et al., *pepuchido gosei no kiso to jikken* [Base and Experiment of Peptide Synthesis]: Maruzen, published Jan. 20, 1985) with the foregoing 3-phenylpropionaldehyde derivatives or cinnamaldehyde derivatives and a reducing agent (for example, NaB(OAc)$_3$H) (refer to A. F. Abdel-Magid et al., Tetrahedron Letters, 31, 5595 (1990)) and thereafter removing the protecting group therefrom, or a method in which an unsaturated bond is saturated with a reducing agent as required. However, the process for producing the compounds of the present invention is not limited thereto. Of course, their acetals or the like can be used as an aldehyde component in the reductive alkylation instead of the foregoing 3-phenylpropionaldehyde derivatives or cinnamaldehyde derivatives.

As a result of an organoleptic (sensory) test, it was found that the derivatives of the present invention, namely, the compounds and those in the form of salts in the present invention had a quality of sweet taste similar to that of sugar and a strong sweetness. For example, a sweetening potency of N-[N-[3-(3,4-dihydroxyphenyl)-3-methylbutyl]-L-α-aspartyl]-L-phenylalanine 1-methyl ester was approximately 50,000 times (relative to sugar), and a sweetening potency of N-[N-[3-(3,4,5-trihydroxyphenyl)propyl]-L-α-aspartyl]-L-phenylalanine 1-methyl ester was approximately 25,000 times (relative to sugar).

The structures and the results of the sensory test on some aspartyl dipeptide ester derivatives (represented by the following general formula (1)) formed are shown in Table 1.

As is clear from the results in Table 1, it is understood that the novel derivatives of the present invention are especially excellent in the sweetening potency.

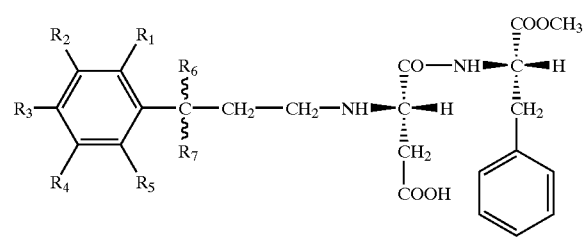

(1)

TABLE 1

Structures and sweetening potencies of aspartyl dipeptide ester derivatives

| Compound No. | R$_1$ | R$_2$ | R$_3$ | R$_4$ | R$_5$ | R$_6$ | R$_7$ | Sweetening potency*) |
|---|---|---|---|---|---|---|---|---|
| 1 | OH | H | OH | H | H | H | H | 10000 |
| 2 | H | OH | OH | H | H | H | H | 15000 |
| 3 | OH | OH | OH | H | H | H | H | 10000 |
| 4 | H | OH | OH | OH | H | H | H | 25000 |
| 5 | H | OH | OH | H | H | CH$_3$ | CH$_3$ | 50000 |

*)Value compared with a 4% sucrose aqueous solution.

Incidentally, when the derivatives of the present invention (including the compounds of the present invention and those in the form of salts) are used as sweeteners, they may naturally be used in combination with other sweeteners unless inviting particular or special troubles.

When the derivatives of the present invention are used as sweeteners, a carrier and/or a filler (bulking agent) may be used as required. For example, a carrier, a filler and the like for sweeteners which have been so far known or used are available.

The derivatives of the present invention can be used as sweeteners or sweetener ingredients, and further as sweetness-imparting ingredients of various products such as food and drink and the like required to have a sweetness (sweet taste), for example, confectionery, chewing gum, sanitary (hygiene) products, toiletries (cosmetics), pharmaceuticals, products for animals except humans, and so forth. The derivatives of the present invention can also be used in the form of sweetened products or in methods for imparting sweetness to products required to have sweetness. Conventional methods for sweetening products may be used.

EXAMPLES

The present invention is illustrated specifically below by referring to Examples. However, the scope of the present invention is not limited to that of the following Examples.

The NMR spectrum was measured with Varian Gemini-300 (300 MHz) and the MS spectrum with Thermo Quest TSQ 700.

Example 1

Synthesis of N-[N-[3-(2,4-dihydroxyphenyl)propyl]-L-α-aspartyl]-L-phenylalanine 1-methyl Ester Ten milliliters of a 4N-HCl/dioxane solution was added to 1.07 g (2.20 mmol) of N-t-butoxycarbonyl-β-O-benzyl-L-α-aspartyl-L-phenylalanine methyl ester, and the mixture was stirred at room temperature for 1 hour. The resulting reaction solution was concentrated in vacuo, and 50 ml of a 5% sodium hydrogencarbonate aqueous solution was added to the residue. The solution was extracted twice with 50 ml of ethyl acetate. An organic layer was washed with a saturated aqueous solution of sodium chloride, and dried over anhydrous magnesium sulfate. Magnesium sulfate was then removed by filtration, and the filtrate was concentrated in vacuo to obtain 780 mg (2.03 mmol) of β-O-benzyl-L-α-aspartyl-L-phenylalanine methyl ester as viscous oil.

The foregoing β-O-benzyl-L-α-aspartyl-L-phenylalanine methyl ester (780 mg, 2.03 mmol) was dissolved in 20 ml of tetrahydrofuran (THF), and this solution was maintained at 0° C. To this were added 689 mg (2.00 mmol) of 3-(2,4-dibenzyloxyphenyl)-2-propenylaldehyde, 0.11 ml (2.00 mmol) of acetic acid and 636 mg (3.00 mmol) of NaB(OAc)$_3$H, and the mixture was stirred at 0° C. for 1 hour and further overnight at room temperature. To the resulting reaction solution was added 50 ml of a saturated aqueous solution of sodium hydrogencarbonate, and the solution was extracted twice with 50 ml of ethyl acetate. An organic layer was washed with a saturated aqueous solution of sodium chloride, and dried over anhydrous magnesium sulfate. Magnesium sulfate was then removed by filtration, and the filtrate was concentrated in vacuo. The residue was purified by preparative thin layer chromatography (PTLC) to obtain 937 mg (1.31 mmol) of N-[N-[3-(2,4-dibenzyloxyphenyl)-2-propenyl]-β-O-benzyl-L-α-aspartyl]-L-phenylalanine 1-methyl ester as viscous oil.

The foregoing N-[N-[3-(2,4-dibenzyloxyphenyl)-2-propenyl]-β-O-benzyl-L-α-aspartyl]-L-phenylalanine 1-methyl ester (937 mg, 1.31 mmol) was dissolved in a mixed solvent of 30 ml of methanol and 2 ml of water, and 400 mg of 10% palladium carbon (water content 50%) was added thereto. This was reduced in a hydrogen atmosphere at room temperature for 3 hours. The catalyst was removed by filtration, and the filtrate was concentrated in vacuo. The resulting residue was purified by PTLC to obtain 378 mg (0.85 mmol) of N-[N-[3-(2,4-dihydroxyphenyl)propyl]-L-α-aspartyl]-L-phenylalanine 1-methyl ester as a solid.

$^1$HNMR (DMSO-d6) δ: 1.46–1.58 (m, 2H), 2.14–2.40 (m, 6H), 2.60–2.98 (m, 1H), 3.02–3.12 (m, 1H), 3.38–3.48 (m,

1H), 3.62 (s, 3H), 4.52–4.62 (m, 1H), 6.11 (d, 1H), 6.25 (s, 1H), 6.75 (d, 1H), 7.18–7.28 (m, 5H), 8.55 (brd, 1H), 8.95 (brs, 2H).

ESI-MS 445.3 (MH$^+$)

Sweetening potency (relative to sugar) 10,000 times

Example 2

Synthesis of N-[N-[3-(3,4-dihydroxyphenyl)propyl]-L-α-aspartyl]-L-phenylalanine 1-methyl Ester N-[N-[3-(3,4-dihydroxyphenyl)propyl]-L-α-aspartyl]-L-phenylalanine 1-methyl ester was obtained as a solid in a total yield of 52.3% in the same manner as in Example 1 except that 3-(3,4-dibenzyloxyphenyl)-2-propenylaldehyde was used instead of 3-(2,4-dibenzyloxyphenyl)-2-propenylaldehyde.

$^1$HNMR (DMSO-d6) δ: 1.48–1.57 (m, 2H), 2.40–2.80 (m, 6H), 2.91 (dd, 1H), 3.06 (dd, 1H), 3.37–3.43 (m, 1H), 3.62 (s, 3H), 4.52–4.62 (m, 1H), 6.39 (d, 1H), 6.54 (s, 1H), 6.61 (d, 1H), 7.18–7.28 (m, 5H), 8.50 (d, 1H), 8.62 (brs, 2H).

ESI-MS 445.2 (MH$^+$)

Sweetening potency (relative to sugar) 15,000 times

Example 3

Synthesis of N-[N-[3-(2,3,4-trihydroxyphenyl)propyl]-L-α-aspartyl]-L-phenylalanine 1-methyl Ester N-[N-[3-(2,3,4-trihydroxyphenyl)propyl]-L-α-aspartyl]-L-phenylalanine 1-methyl ester was obtained as a solid in a total yield of 32.7% in the same manner as in Example 1 except that 3-(2,3,4-tribenzyloxyphenyl)-2-propenylaldehyde was used instead of 3-(2,4-dibenzyloxyphenyl)-2-propenylaldehyde.

$^1$HNMR (DMSO-d6) δ: 1.48–1.62 (m, 2H), 2.16–2.45 (m, 6H), 2.87–2.98 (m, 1H), 3.02–3.12 (m, 1H), 3.40–3.50 (m, 1H), 3.61 (s, 3H), 4.50–4.60 (m, 1H), 6.19 (d, 1H), 6.29 (d, 1H), 7.15–7.31 (m, 5H), 8.57 (d, 1H), 8.75 (brs, 1H).

ESI-MS 461.2 (MH$^+$)

Sweetening potency (relative to sugar) 10,000 times

Example 4

Synthesis of N-[N-[3-(3,4,5-trihydroxyphenyl)propyl]-L-α-aspartyl]-L-phenylalanine 1-methyl Ester N-[N-[3-(3,4,5-trihydroxyphenyl)propyl]-L-α-aspartyl]-L-phenylalanine 1-methyl ester was obtained as a solid in a total yield of 26.1% in the same manner as in Example 1 except that 3-(3,4,5-tribenzyloxyphenyl)-2-propenylaldehyde was used instead of 3-(2,4-dibenzyloxyphenyl)-2-propenylaldehyde.

$^1$HNMR (DMSO-d6) δ: 1.44–1.56 (m, 2H), 2.14–2.34 (m, 6H), 2.93 (dd, 1H), 3.10 (dd, 1H), 3.30–3.45 (m, 1H), 3.62 (s, 3H), 4.50–4.62 (m, 1H), 6.07 (s, 2H), 7.15–7.29 (m, 5H), 8.51 (brs, 1H), 8.65 (brs, 1H).

ESI-MS 461.2 (MH$^+$)

Sweetening potency (relative to sugar) 25,000 times

Example 5

Synthesis of N-[N-[3-(3,4-dihydroxyphenyl)-3-methylbutyl]-L-α-aspartyl]-L-phenylalanine 1-methyl Ester N-[N-[3-(3,4-dihydroxyphenyl)-3-methylbutyl]-L-α-aspartyl]-L-phenylalanine 1-methyl ester was obtained as a solid in a total yield of 76.5% in the same manner as in Example 1 except that 3-(3,4-dibenzyloxyphenyl)-3-methylbutylaldehyde was used instead of 3-(2,4-dibenzyloxyphenyl)-2-propenylaldehyde.

$^1$HNMR (DMSO-d6) δ: 1.44 (s, 6H), 1.76–1.93 (m, 2H), 2.40–2.50 (m, 2H), 2.73–2.80 (m, 2H), 2.91 (dd, 1H), 3.06 (dd, 1H), 3.59 (s, 3H), 3.95–4.05 (m, 1H), 4.45–4.55 (m, 1H), 6.52 (d, 1H), 6.64–6.70 (m, 2H), 7.15–7.30 (m, 5H), 8.73 (brs, 1H), 8.80 (brs, 1H), 8.90 (brs, 1H), 9.09 (brs, 1H).

ESI-MS 473.2 (MH$^+$)

Sweetening potency (relative to sugar) 50,000 times

Effects of the Invention

The novel aspartyl dipeptide ester derivatives of the present invention are low-calorie, and have a sweet taste excellent in a sweetening potency in particular in comparison with ordinary sweeteners. The present invention can provide novel chemical substances useful as sweetener ingredients. Accordingly, the novel derivatives can be used as sweeteners and can also impart a sweetness to products such as foods and drinks and the like requiring sweetness or increased sweetness.

Modifications and Other Embodiments

Various modifications and variations of the described products, compositions, sweeteners, foods, drinks, and methods for their production and use, as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the food, nutritional, chemical, chemical engineering, manufacturing, pharmaceutical, medical, biological or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specifically, PCT/JP00/06627, filed Sep. 26, 2000, and JP 11-281920, filed Oct. 1, 1999, are hereby incorporated by reference.

What is claimed is:

1. An aspartyl dipeptide ester derivative, or a salt thereof, represented by the following formula (1):

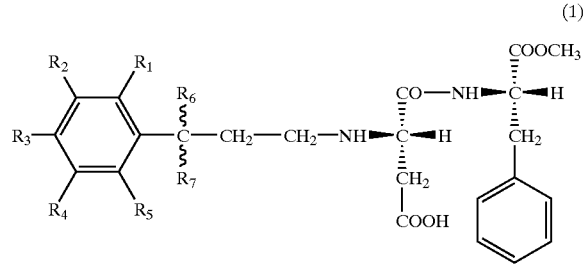

wherein $R_1$, $R_2$, $R_3$, $R_4$ and $R_5$, independently from each other, represent a hydrogen atom or a hydroxyl group, at least any two of $R_1$ to $R_5$ are hydroxyl groups, and $R_6$ and $R_7$, independently from each other, represent a hydrogen atom or an alkyl group having 1 to 3 carbon atoms.

2. The derivative according to claim 1, wherein in the said formula $R_1$ and $R_3$ are hydroxyl groups, and $R_2$, $R_4$, $R_5$, $R_6$ and $R_7$ are hydrogen atoms.

3. The derivative according to claim 1, wherein $R_2$ and $R_3$ are hydroxyl groups, and $R_1$, $R_4$, $R_5$, $R_6$ and $R_7$ are hydrogen atoms.

4. The derivative according to claim 1, wherein $R_1$, $R_2$ and $R_3$ are hydroxyl groups, and $R_4$, $R_5$, $R_6$ and $R_7$ are hydrogen atoms.

5. The derivative according to claim 1, wherein $R_2$, $R_3$ and $R_4$ are hydroxyl groups, and $R_1$, $R_5$, $R_6$ and $R_7$ are hydrogen atoms.

6. The derivative according to claim 1, wherein $R_2$ and $R_3$ are hydroxyl groups, $R_1$, $R_4$ and $R_5$ are hydrogen atoms, and $R_6$ and $R_7$ are methyl groups.

7. The compound of claim 1 where $R_6$ and $R_7$ are different and the steric configuration of the carbon atom to which these substituents are bound is (R).

8. The compound of claim 1 where $R_6$ and $R_7$ are different and the steric configuration of the carbon atom to which these substituents are bound is (S).

9. A mixture comprising the compound of claim 1 where $R_6$ and $R_7$ are different and the steric configuration of the carbon atom to which these substituents are bound is (R) and (S).

10. The compound of claim 1, wherein the aspartic acid moiety is the L-isomer.

11. The compound of claim 1, wherein the phenylalanine moiety is the L-isomer.

12. The compound of claim 1 that is a salt.

13. The compound of claim 1 that is an alkali metal salt.

14. The compound of claim 1 that is an alkaline earth metal salt.

15. The compound of claim 1 that is an ammonium salt.

16. The compound of claim 1 that is a salt of an organic acid.

17. The compound of claim 1 that is a salt of an inorganic acid.

18. The compound of claim 1 that is a salt of another sweetener.

19. A composition comprising the derivative according to claim 1.

20. The composition of claim 19, further comprising one or more other sweetener(s).

21. The composition of claim 19 that is a sweetener, and that may optionally further comprise a carrier or filler.

22. The composition of claim 19 that is a food.

23. The composition of claim 19 that is a drink.

24. The composition of claim 19 that is a pharmaceutical product.

25. The composition of claim 19 that is a sanitary product, toiletry, or cosmetic.

26. A method for sweetening a product comprising adding the derivative of claim 1 to said product or to an intermediate ingredient used to produce said product.

27. The method of claim 26 that comprises adding said derivative to a product during the production stage thereof.

28. A method for making a compound of formula (1):

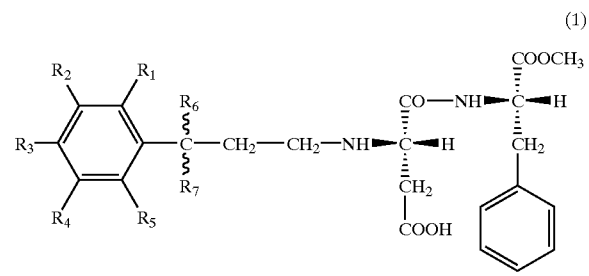

wherein:

$R_1$, $R_2$, $R_3$, $R_4$ and $R_5$, each independently represent a hydrogen atom or a hydroxyl group, at least two of $R_1$ to $R_5$ are hydroxyl groups, and $R_6$ and $R_7$, each independently represent a hydrogen atom or an alkyl group having 1 to 3 carbon atoms;

comprising:

reductively alkylating aspartame with a 3-phenylpropionaldehyde or cinnamaldehyde derivative and a reducing agent.

* * * * *